US011511037B2

(12) United States Patent
Deliwala

(10) Patent No.: US 11,511,037 B2
(45) Date of Patent: Nov. 29, 2022

(54) SYSTEMS AND METHODS FOR MEASURING NEEDLE DEPTH

(71) Applicant: Analog Devices, Inc., Norwood, MA (US)

(72) Inventor: Shrenik Deliwala, Andover, MA (US)

(73) Assignee: Analog Devices, Inc., Wilmington, MA (US)

( * ) Notice: Subject to any disclaimer, the term of this patent is extended or adjusted under 35 U.S.C. 154(b) by 161 days.

(21) Appl. No.: 16/434,761

(22) Filed: Jun. 7, 2019

(65) Prior Publication Data

US 2019/0374711 A1 Dec. 12, 2019

Related U.S. Application Data

(60) Provisional application No. 62/682,737, filed on Jun. 8, 2018.

(51) Int. Cl.
*A61M 5/168* (2006.01)
*A61B 5/15* (2006.01)
(Continued)

(52) U.S. Cl.
CPC ....... *A61M 5/16836* (2013.01); *A61B 5/0531* (2013.01); *A61B 5/150389* (2013.01);
(Continued)

(58) Field of Classification Search
CPC ............... A61M 5/16836; A61M 5/46; A61B 5/150389; A61B 90/06; A61B 5/6848;
(Continued)

(56) References Cited

U.S. PATENT DOCUMENTS 5,586,553 A 12/1996 Halili et al.
6,206,875 B1 3/2001 Long et al.
(Continued)

FOREIGN PATENT DOCUMENTS

DE 19914485 C2 * 10/2002 ............. A61M 5/46
JP 2003279349 10/2003
(Continued)

OTHER PUBLICATIONS

International Search Report and Written Opinion mailed in PCT Patent Application Serial No. PCT/US2019/036191 dated Jan. 6, 2020, 18 pages.
(Continued)

*Primary Examiner* — James D Ponton
*Assistant Examiner* — Neeraja Gollamudi
(74) *Attorney, Agent, or Firm* — Akona IP PC

(57) ABSTRACT

Systems and methods are provided for measuring depth, position, and/or angle of a cannula in a medical drug delivery device. In particular, a drug delivery device having a cannula is positioned adjacent to tissue, a voltage pulse is provided to the cannula, a charge is measured at an electrode in the drug delivery device, and the depth of penetration of the cannula is determined based in part on the charge at the first electrode. Systems and methods described herein can be used to determine subcutaneous insertion depth in a wearable bolus injector. In some implementations, insertion depth determination is achieved through capacitive sensors which measure needle depth in a drug delivery device.

20 Claims, 12 Drawing Sheets

(51) Int. Cl.
*A61B 90/00* (2016.01)
*A61B 5/00* (2006.01)
*A61B 5/0531* (2021.01)
*A61M 5/142* (2006.01)

(52) U.S. Cl.
CPC .......... *A61B 5/6833* (2013.01); *A61B 5/6843* (2013.01); *A61B 5/6848* (2013.01); *A61B 90/06* (2016.02); *A61M 5/14248* (2013.01); *A61B 5/4839* (2013.01); *A61B 2090/062* (2016.02); *A61M 2205/13* (2013.01)

(58) Field of Classification Search
CPC ................ A61B 5/0531; A61B 5/6833; A61B 2090/062; A61B 5/483; A61B 5/4839; A61B 5/159175
See application file for complete search history.

(56) References Cited

U.S. PATENT DOCUMENTS

| | | | |
|---|---|---|---|
| 6,951,549 B1* | 10/2005 | Beyerlein | A61B 5/053 604/117 |
| 7,106,574 B2 | 9/2006 | Beyerlein | |
| 7,147,615 B2 | 12/2006 | Wariar et al. | |
| 8,016,774 B2 | 9/2011 | Freeman et al. | |
| 9,173,697 B2 | 11/2015 | Morrissette et al. | |
| 9,872,633 B2 | 1/2018 | Limaye et al. | |
| 10,105,040 B2 | 10/2018 | Ochi et al. | |
| 2005/0154434 A1* | 7/2005 | Simon | A61M 5/422 607/116 |
| 2009/0036794 A1* | 2/2009 | Stubhaug | A61B 5/416 600/547 |
| 2009/0088662 A1* | 4/2009 | Larsen | A61M 5/16836 600/547 |
| 2011/0105942 A1* | 5/2011 | Lim | A61B 5/685 600/547 |
| 2013/0253447 A1* | 9/2013 | Ball | A61M 5/14276 604/288.01 |
| 2016/0089056 A1* | 3/2016 | Limaye et al. | A61B 5/063 600/409 |
| 2017/0281877 A1* | 10/2017 | Marlin | A61M 5/3234 |
| 2018/0014787 A1 | 1/2018 | Ganton et al. | |
| 2018/0103870 A1 | 4/2018 | Limaye et al. | |
| 2019/0059731 A1 | 2/2019 | Peterson | |

FOREIGN PATENT DOCUMENTS

WO WO2006067217 6/2006
WO WO-2015168391 A1 * 11/2015 ........... A61B 5/6852

OTHER PUBLICATIONS

English Abstract of JP2003279349, 1 page.
*Wearable Injectiors*, Sensile Medical, Sep. 19, 2016, Issue No. 70, 48 pages.

\* cited by examiner

SYSTEMS AND METHODS FOR MEASURING NEEDLE DEPTH

CROSS-REFERENCE TO RELATED APPLICATION

This application claims priority to Provisional Patent Application No. 62/682,737 filed on Jun. 8, 2018 and titled "Systems and Methods for Measuring Needle Depth", which is hereby incorporated by reference in its entirety. This application is related to U.S. patent application Ser. No. 14/808,148 entitled, "Circuit architecture for mode switch" filed on Jul. 24, 2015, now U.S. Pat. No. 9,733,275, which is hereby incorporated by reference in its entirety.

FIELD OF THE DISCLOSURE

The present disclosure relates to medical devices using needles or cannulas.

BACKGROUND

Continuous subcutaneous drug therapies comprise small wearable devices which automatically administer drugs to a patient through a needle or cannula. A cannula is a tube that can be inserted into the body, often for the delivery or removal of fluid or for the gathering of data. In simple terms, a cannula can surround the inner or outer surfaces of a trocar needle thus extending the effective needle length by at least half the length of the original needle.

An example of one of these devices is an insulin pump. An insulin pump is a medical device used for the administration of insulin in the treatment of diabetes mellitus, also known as continuous subcutaneous insulin therapy. The device configuration may vary depending on design. A traditional pump comprises a pump (including controls, processing module, and batteries), a disposable reservoir for insulin (inside the pump), and a disposable infusion set, including a cannula for subcutaneous insertion (under the skin).

The medication in the present example is referred to as a bolus. In medicine, a bolus is the administration of a discrete amount of medication, drug, or other compound within a specific time, generally within 1-30 minutes, in order to raise its concentration in blood to an effective level. The administration can be given by injection: intravenously, intramuscularly, intrathecally, subcutaneously, or by inhalation.

The placement of the bolus dose depends on the systemic levels of the contents desired throughout the body. An intramuscular injection of vaccines allows for a slow release of the antigen to stimulate the body's immune system and to allow time for developing antibodies. Subcutaneous injections are used by heroin addicts (called 'skin popping', referring to the bump formed by the bolus of heroin), to sustain a slow release that staves off withdrawal symptoms without producing euphoria.

A bolus delivered directly to the veins through an intravenous drip allows a much faster delivery which quickly raises the concentration of the substance in the blood to an effective level. This is typically done at the beginning of a treatment or after a removal of medicine from blood (e.g. through dialysis).

Accurate cannula positioning and depth insertion is of paramount importance, particularly in the context of wearable injector. For example, in the present state of the art, there is no way to know if a needle or cannula has reached a subcutaneous depth. Consequently, the device has no positive feedback nor confirmation that the drug therapy was properly administered.

SUMMARY OF THE DISCLOSURE

Systems and methods are provided for determining cannula and/or needle depth and position while keeping within certain limiting parameters, specifications, and medical standards. Systems and methods are provided for measuring depth, position, and/or orientation in a medical drug delivery device. The present disclosure contemplates measuring a cannula insertion which can also provide clear feedback on the insertion depth. For example, systems and methods described herein can determine subcutaneous insertion depth in a wearable bolus injector. In some implementations, insertion depth determination is achieved through capacitive sensors which measure needle depth in a bolus injector.

A baseline can be established by measuring the self-capacitance of the device and/or the patient. In some implementations, a plurality of capacitive sensors can measure the mutual capacitance of other sensors, the cannula, the device and body. A positional determination can then be made. These measurements can be used to determine needle depth information as well as needle position. Subsequent to affirmation of needle depth and position, the drug delivery unit is signaled to begin therapy.

According to one aspect, the present disclosure is a wearable drug delivery apparatus comprising a self-capacitance measuring circuit connected to the conducting cannula in which the measured output of the circuit is related to the contact to the skin as well as to the penetration depth.

According to another aspect, a system for sensing cannula penetration depth in a drug delivery device, comprises a cannula, configured for insertion into the tissue, a first circuit configured to provide a voltage pulse to the cannula, a first electrode, spaced apart from the cannula, a mutual-capacitance circuit configured to measure a change in a first charge at the first electrode, and a processor configured to determine a depth of penetration of the cannula based at least in part on the change in the first charge at the first electrode. The cannula is conductive.

According to one implementation, the mutual-capacitance circuit measures a first capacitance from the first electrode, and the processor is configured to determine the depth of penetration of the cannula based at least in part on the first capacitance.

In one implementation, the system further includes a second electrode, spaced apart from the first electrode and the cannula, having a second charge. In some implementations, the mutual-capacitance circuit is further configured to measure a second capacitance from the second electrode, and the processor is further configured to determine the depth of penetration of the cannula based at least in part on the second capacitance.

According to some implementations, the first electrode is divided into at least two sections, and the mutual-capacitance circuit determines a section-capacitance for each of the at least two sections. In some implementations, the processor is configured to determine an angle of penetration of the cannula based at least in part on the section-capacitances of the at least two sections.

In some implementations, the cannula is comprised of a conductive metal. In some implementations, the cannula is comprised of a non-conducting material and is coated with a layer of conducting material.

According to various implementations, the system for sensing cannula penetration depth in a drug delivery device further comprises a self-capacitance circuit configured to measure a change in cannula capacitance, wherein the processor is further configured to determine the depth of penetration of the cannula based at least in part on the cannula capacitance.

In one implementation, the first electrode surrounds the cannula.

According to another aspect, a method for determining penetration depth of a cannula comprises positioning a drug delivery device including the cannula adjacent to tissue, providing a voltage pulse to the cannula, measuring a charge at a first electrode of the drug delivery device, and determining a depth of penetration of the cannula based at least in part on the charge at the first electrode.

In some implementations, the method further comprises measuring a second charge at a second electrode, wherein the second electrode is spaced apart from the first electrode and the cannula. In some implementations, determining the depth of penetration of the cannula is based at least in part on the second charge at the second electrode.

According to various implementations, the method further includes determining a first capacitance from the first electrode to the cannula, determining a second capacitance from the second electrode to the cannula, and determining the depth of penetration based at least in part on the first and second capacitances.

In some implementations, the method includes measuring a change in cannula capacitance, and determining the depth of penetration of the cannula based at least in part on the change in cannula capacitance In some implementations, the method includes measuring a self-capacitance of the first electrode, and determining whether the drug delivery device is positioned adjacent to tissue, based at least in part on the self-capacitance of the first electrode.

According to some aspects, a drug delivery apparatus for injecting a drug into tissue includes a cannula, configured for insertion into the tissue, a self-capacitance measuring circuit connected to the cannula for measuring a self-capacitance of the cannula, and a processor configured to determine the depth of penetration of the cannula based on the self-capacitance of the cannula. The self-capacitance measuring circuit includes an amplifier and a voltage pulse, and the amplifier is connected to the cannula and measures a charge from the cannula. The cannula is conductive.

In some implementations, the apparatus further comprises a series resistor and/or a capacitor, connected between the cannula and the amplifier.

In some implementations, the apparatus further comprises a mutual-capacitance measuring circuit. In various implementations, the apparatus includes a first electrode, the mutual-capacitance circuit measures a capacitance at the first electrode, and the processor is further configured to determine the depth of the cannula based at least in part on the capacitance at the first electrode.

According to another aspect, the present disclosure is a wearable drug delivery apparatus wherein measurement of the self-capacitance of other electrodes (not cannula) is used to provide information on whether the drug delivery apparatus is attached to the body before beginning auto-injector cycle.

According to another aspect, the present disclosure is a wearable drug delivery apparatus, wherein the device continues to monitor the capacitance to determine dispersion of the drug/biologic into the body, in any of the previous aspects or implementations.

The drawings show exemplary bolus injector, circuits and configurations. Variations of these circuits, for example, changing the positions of, adding, or removing certain elements from the circuits are not beyond the scope of the present invention. The illustrated smoke detectors, configurations, and complementary devices are intended to be complementary to the support found in the detailed description.

This overview is intended to provide an overview of subject matter of the present patent application. It is not intended to provide an exclusive or exhaustive explanation of the invention. Further limitations and disadvantages of conventional and traditional approaches will become apparent to one of skill in the art, through comparison of such systems with some aspects of the present invention as set forth in the remainder of the present application with reference to the drawings.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

Figure 1:
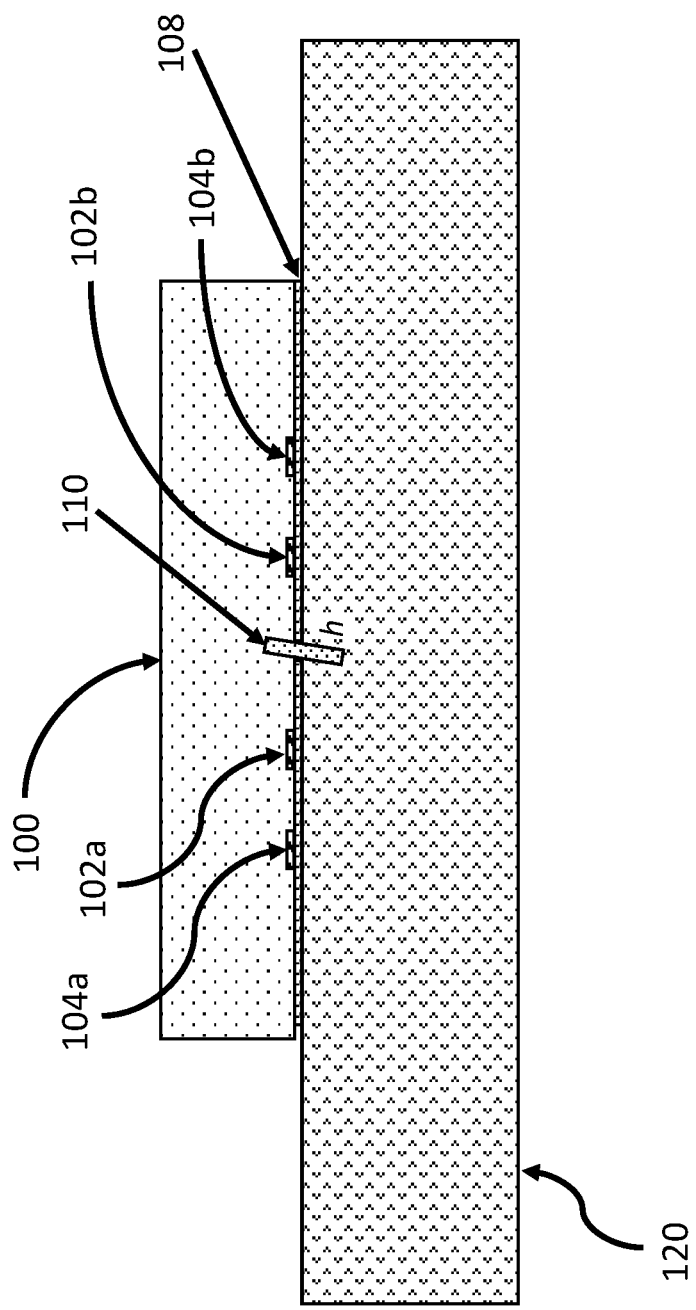
FIG. 1 is an exemplary wearable drug delivery device, in accordance with some embodiments of the disclosure provided herein.

The present disclosure relates to medical devices using needles or cannulas. More specifically, this disclosure describes apparatus and techniques relating to measuring the needle and/or cannula depth in a patient during drug delivery.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

In one or more implementations, capacitive sensors measure needle depth in a bolus injectable. A baseline can be established by measuring the self-capacitance of the device and/or the patient. In some embodiments, a plurality of capacitive sensors can measure the mutual capacitance of the other sensors, the cannula, the device, and the body. The measurements can be used to calculate a positional determination. These measurements can be used to determine needle (or cannula) depth information and needle (or cannula) position. Following determination of acceptable cannula/needle depth and position, the drug delivery unit is signaled to begin drug delivery. Presently, this is a primary demand in the state of the art.

It is well established that automated wearable drug delivery systems or wearable bolus injectors (BI) are necessary for some new classes of drugs. For example, wearable systems are used for drugs that are delivered subcutaneously and in high volumes. In another example, wearable systems are used for viscous drugs. In various examples, some drugs require adherence to a specified regimen for high efficacy, and the regimen is most easily and consistently followed when the drugs are delivered via a wearable drug delivery system or wearable bolus injector.

In automated injectors, a microprocessor controlled system is used to deliver the drug at a predetermined time. A needle or cannula is automatically inserted into the tissue and drug delivered by a built-in pump. Many such systems are in the market such as Beckton-Dickenson (BD) Libertas and many others.

The market for wearable automated drug delivery systems is expected grow quite dramatically as more and more treatments for cancer treatment and immune system disorders such as Rheumatoid Arthritis and multiple sclerosis include delivery of biologics. A biologic is any pharmaceutical drug product manufactured in, extracted from, or semisynthesized from, a biological source. Different from totally synthesized pharmaceuticals, biologics include vaccines, blood, blood components, allergenics, somatic cells, gene therapies, tissues, recombinant therapeutic protein, and living cells used in cell therapy. In some examples, biologics are composed of sugars, proteins, nucleic acids, and/or complex combinations of these substances. In some examples, biologics are composed of living cells and/or tissues. Biologics (or their precursors or components) are isolated from living sources. Living sources that biologics may be isolated from include human sources, animal sources, plant sources, fungal sources, and microbial sources.

Most of the drug delivery systems available on the market today assume that the mechanical design is robust enough to guarantee insertion of the cannula to the desired depth before beginning the dosing phase. However, this is not guaranteed in current drug delivery systems. It is extremely important to find a robust method that positively measures the cannula insertion and also provides clear feedback on the insertion depth. Many bolus injection systems are returned due to failure of the cannula to insert properly. Similarly, many patient complaints of bolus injection systems revolve around failure of the cannula to insert properly. Improper cannula insertion leads to waste of very expensive biologics and low level of patient satisfaction. Failure of the cannula to insert properly also defeats the very purpose for which these systems are used in the first place—a good reliable administration of biologics and adherence to the regimen as prescribed.

Systems and methods presented herein offer direct feedback on the cannula insertion as well as determination of cannula depth. In some implementations, the systems and methods provide information on the angle of insertion of the cannula. In one or more implementations, systems and methods of the present disclosure include techniques to measure the cannula depth. In some implementations, systems and methods are disclosed for techniques to positively measure of insertion of the cannula into the tissue. While the techniques are closely related, they are not dependent on each other. Thus, one technique can be used without the other.

One technique for measurement of cannula depth and positive measure of insertion of a cannula into tissue is self-capacitance (SC) of the cannula. Another technique for measurement of cannula depth and positive measure of insertion of a cannula into tissue is mutual-capacitance (MC) of the cannula measured with respect to patterned electrodes surrounding the cannula.

Both techniques can provide a measurement for cannula depth. According to some implementations, the mutual-capacitance technique may provide a more accurate measurement of cannula depth. Additionally, the mutual-capacitance technique can provide information about the angle of insertion.

FIG. 1 is an exemplary wearable drug delivery device 100, in accordance with some embodiments of the disclosure. The drug delivery device 100 includes a first set of electrodes 102a, 102b, a second set of electrodes 104a, 104b, and a cannula 110. The drug delivery device 100 is shown positioned adjacent to tissue 120. In various examples, the cannula 110 of the drug delivery device 100 can penetrate the surface of the tissue 120, and a drug can be injected into the tissue 120. In various examples, the drug delivery device 100 injects a bolus into the tissue 120. In some examples, the drug delivery device 100 injects a bolus subcutaneously.

According to various implementations, the drug delivery device 100 includes an adhesive element 108. The adhesive element 108 is positioned on a bottom side of the drug delivery device 100, and the bottom side is designed for placement on a person's skin. Thus, the adhesive element 108 can be used to secure the drug delivery device 100 to a wearer's skin.

The first 102a, 102b and second 104a, 104b electrodes are positioned around the cannula 110. As shown in FIG. 1, the first 102a, 102b and second 104a, 104b electrodes are positioned underneath the adhesive element 108. The first 102a, 102b and second 104a, 104b electrodes and the cannula 110 are connected to an electrical measurement system inside the drug delivery device 100. The electrical measurement system uses measurements from the first 102*a*, 102*b* and second 104*a*, 104*b* electrodes to determine the position and depth of the cannula 110.

In some implementations, in the drug delivery device 100, self-capacitance measurements are used to determine cannula 110 depth. In other implementations, in the drug delivery device 100, mutual-capacitance measurements are used to determine cannula 110 depth. In some implementations, both self-capacitance measurements and mutual capacitance measurements are used to determine a depth of the cannula 110. In some implementations, self-capacitance measurements and mutual capacitance measurements for cannula 110 depth are calculated simultaneously.

Mutual-capacitance measurements can be determined using one set of electrodes. In one example, mutual capacitance measurements are determined using the first set of electrodes 102*a*, 102*b*. In another example, mutual capacitance measurements are determined using the second set of electrodes 104*a*, 104*b*. In another example, mutual capacitance measurements are determined using the first 102*a*, 102*b* and second 104*a*, 104*b* sets of electrodes. In some implementations, the first 102*a*, 102*b* and second 104*a*, 104*b* sets of electrodes are used to determine an angle of penetration of the cannula 110.

According to various implementations, the drug delivery device 100 includes a processor configured to determine the depth of penetration of the cannula. In one example, the electrical measurement system includes a processor. In some implementations, the drug delivery device 100 is connected to a processor configured to determine a depth of penetration of the cannula. In various implementations, data from one or more of the cannula, the electrodes, and the electrical measurement system is transmitted to the processor, and the processor uses the data to determine the depth of penetration, and/or the position and/or orientation of the cannula. In some examples, the processor is a microprocessor.

Figure 2:
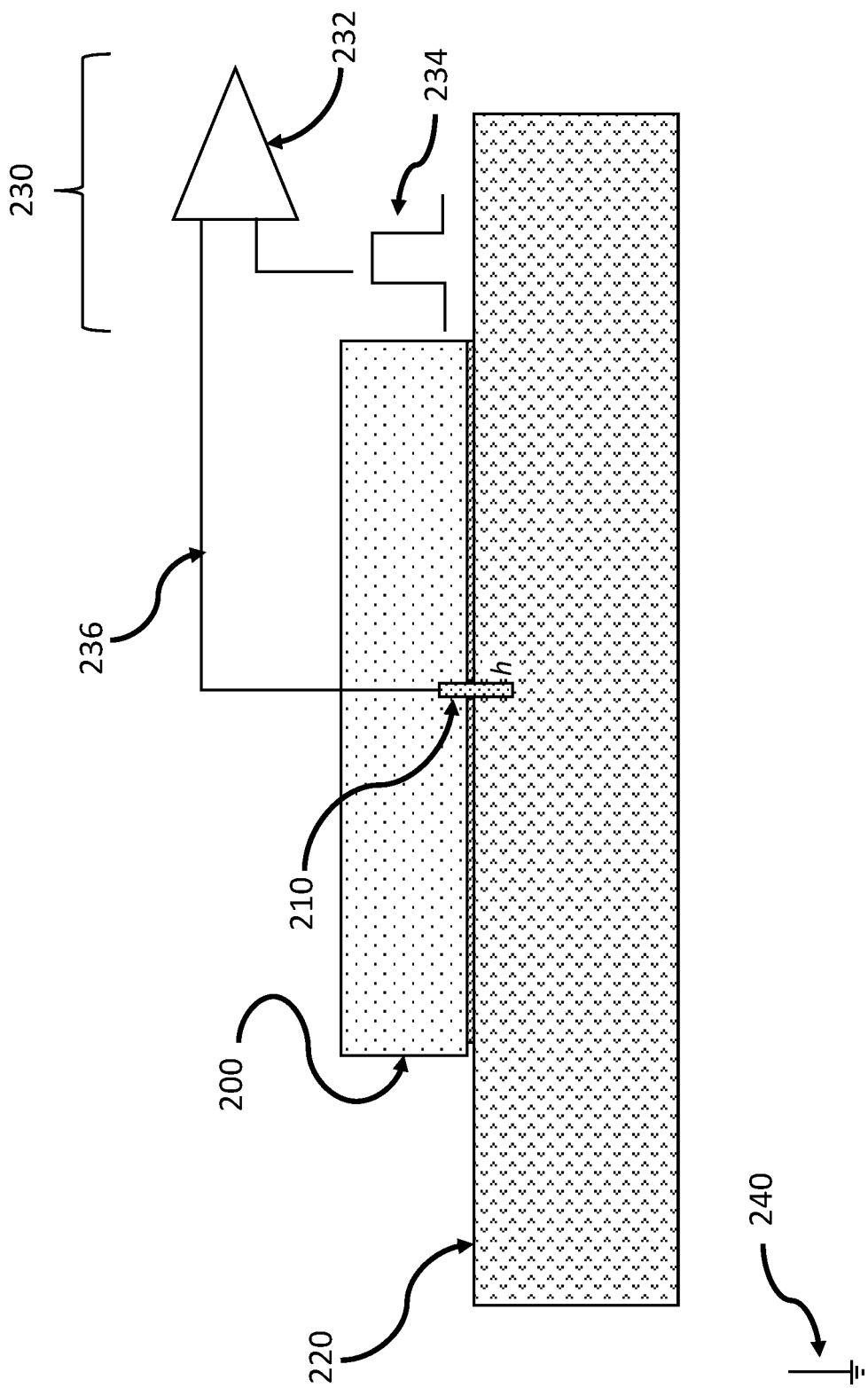
FIG. 2 shows an exemplary wearable drug delivery device including a self-capacitance measuring system, in accordance with some embodiments of the disclosure provided herein.

FIG. 2 shows an exemplary wearable drug delivery device 200 with injector including a self-capacitance measuring system 230, in accordance with some embodiments of the disclosure. In general, self-capacitance of a conducting body can be measured by measuring the total change in charge on the body when its potential is changed by a known voltage. Thus, $$C_{self} = \frac{\delta Q}{\delta V} \quad (1)$$

where Q is the charge and V is the voltage.

The other electrode of the capacitor—in this case the body 220 plus the cannula 210—is assumed to be somewhere near the conductive body (or at infinity). The AC circuit closes through some indirect means to the ground 240 of the measurement circuit. This type of measurement is very sensitive to the nearby ground planes. The self-capacitance measuring system 230 includes an amplifier 232, and a voltage pulse 234. The amplifier 232 measures the charge 236 from the cannula 210.

The average human has a self-capacitance of the order of about 100 pF. A non-touching cannula 210 (a cannula 210 not in contact with a body 220) has very low self-capacitance. Because the cannula 210 alone has a much smaller capacitance than the cannula 210 plus the body 220, it is easy to tell when cannula 210 touches the body 220. As soon as the cannula 210 touches the body 220, the self-capacitance of the cannula 210 (in contact with the body 220) suddenly goes up. This sudden change in the self-capacitance can be used to mark the time at which the cannula 210 touches the body 220. When the cannula 210 penetrates the skin of the body 220 and electrically connects to the subcutaneous layers, the self-capacitance continues to grow. The electrical coupling of the cannula 210 to the body 220 improves with increased insertion. The increase in self-capacitance of the cannula 210 and the body 220 can be used to determine the depth of insertion of the cannula 210.

Figure 3:
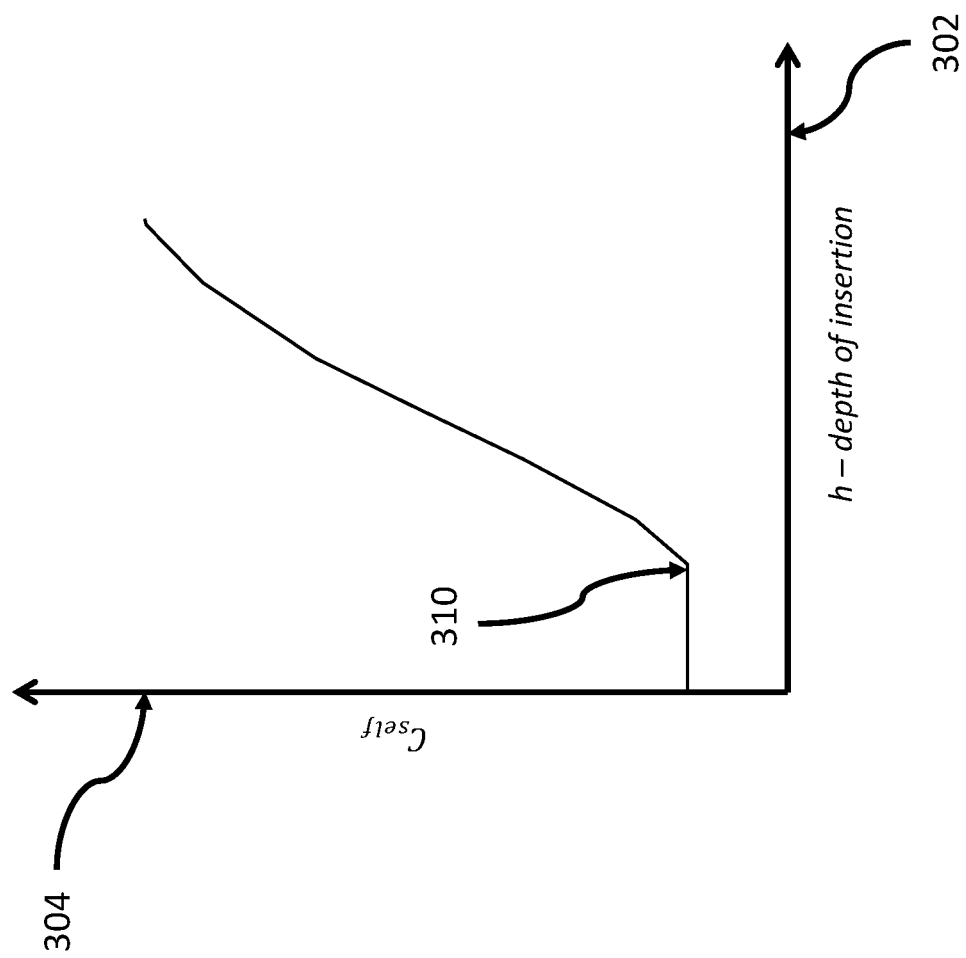
FIG. 3 shows a graph including self-capacitance measurements, in accordance with some embodiments of the disclosure provided herein.

An experiment on self-capacitance measurement of a conductive wire showed increased self-capacitance of the wire as more of the wire was pinched between fingers. In particular, a conductive wire with the approximate diameter of a needle was pinched between the fingers, and as the pinch progressed from just the end of the wire to cover more and more of the wire, the self-capacitance of the wire increased. FIG. 3 is a graph 300 showing measurements of self-capacitance in accordance with some embodiments of the disclosure provided herein. In particular, the graph 300 shows the depth of insertion of the wire between the fingers on x-axis 302 and the self-capacitance of the wire on the y-axis 304. The point 310 is the point at which the wire first contacts the fingers. As shown in the graph 300, the greater the length of wire pinched between the fingers (on the x-axis), the greater the self-capacitance measurement on the y-axis.

Figure 4:
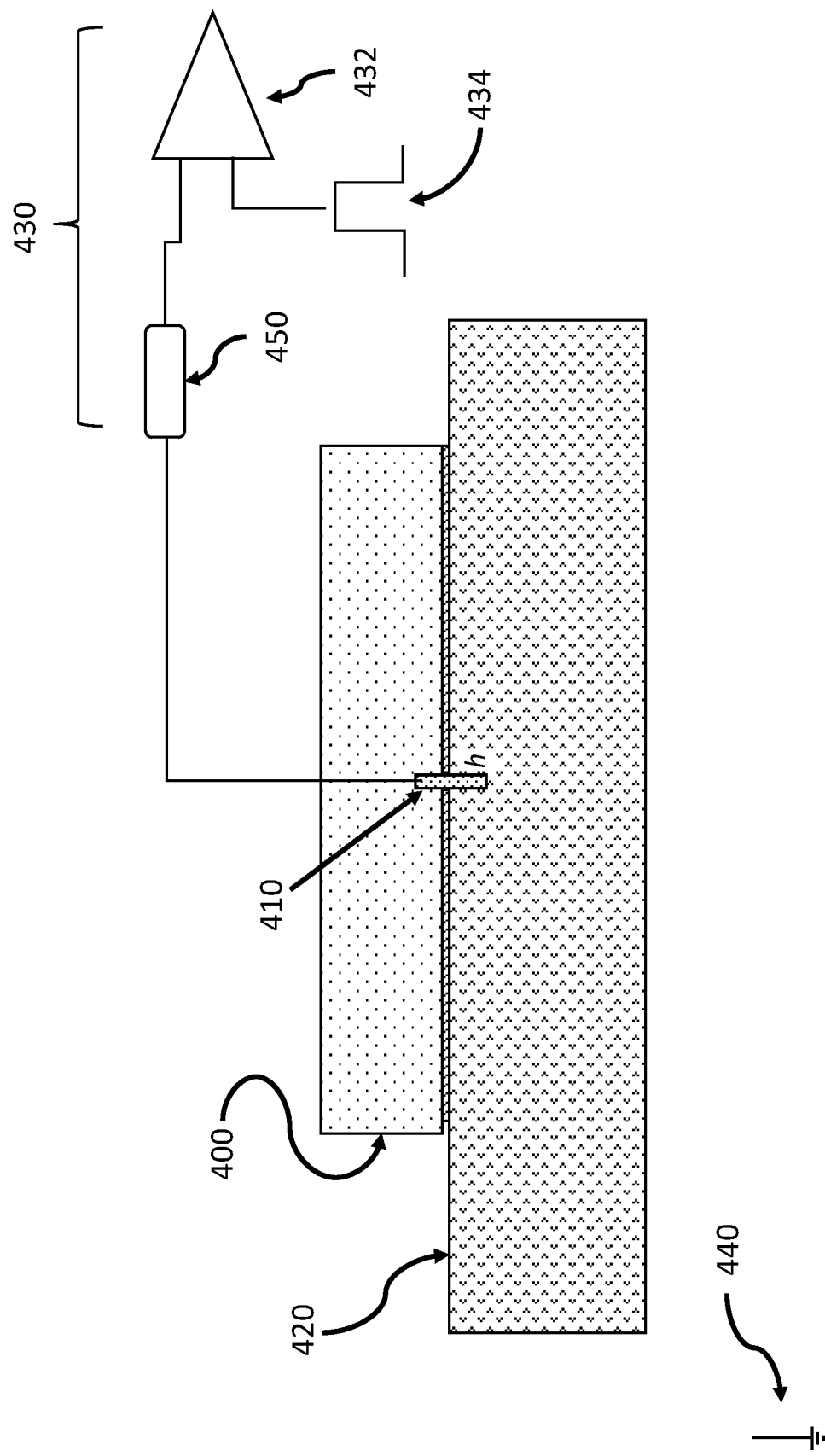
FIG. 4 shows another exemplary wearable drug delivery device including a self-capacitance measuring system, in accordance with some embodiments of the disclosure.

FIG. 4 shows another exemplary wearable drug delivery device 400 with injector including a self-capacitance measuring system 430, in accordance with some embodiments of the disclosure. The self-capacitance measuring system 430 includes a voltage pulse 434, an amplifier 432, and an additional module 450 of one or more electrical components. According to one implementation, the additional electrical component module 450 is designed to prevent large currents from flowing into the body 420. In one example, the additional electrical component module 450 is a series resistor. In another example, the additional electrical component module 450 includes a capacitor.

According to one implementation, the resistance of a series resistor used in the additional electrical component module 450 is:

$$R_s > \frac{\delta V}{I_m} \quad (2)$$

where V is voltage and I is current. The series resistor will prevent currents greater than specified allowed maximum currents. In other implementations, the additional electrical component module 450 is a series capacitor having a much greater capacitance than the self-capacitance of the body 420, which prevents DC currents from flowing into the body 420. Note that the additional electrical component module 450 does not prevent measurement of cannula depth and position.

Figure 5B:
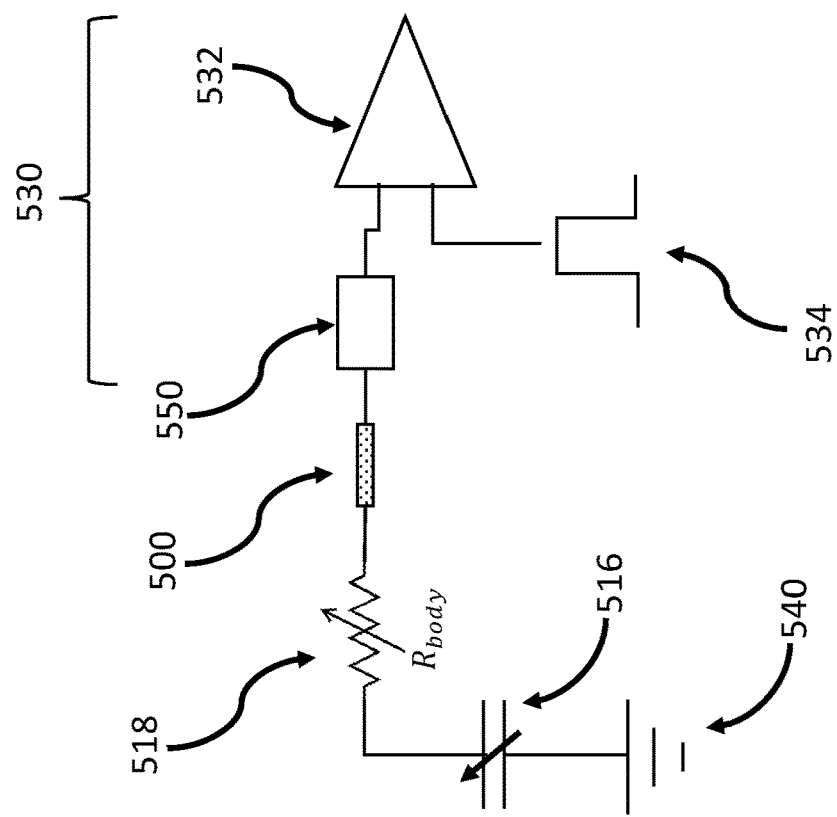
FIG. 5B shows circuit components including the exemplary wearable drug delivery device, in accordance with some embodiments of the disclosure.
Figure 5A:
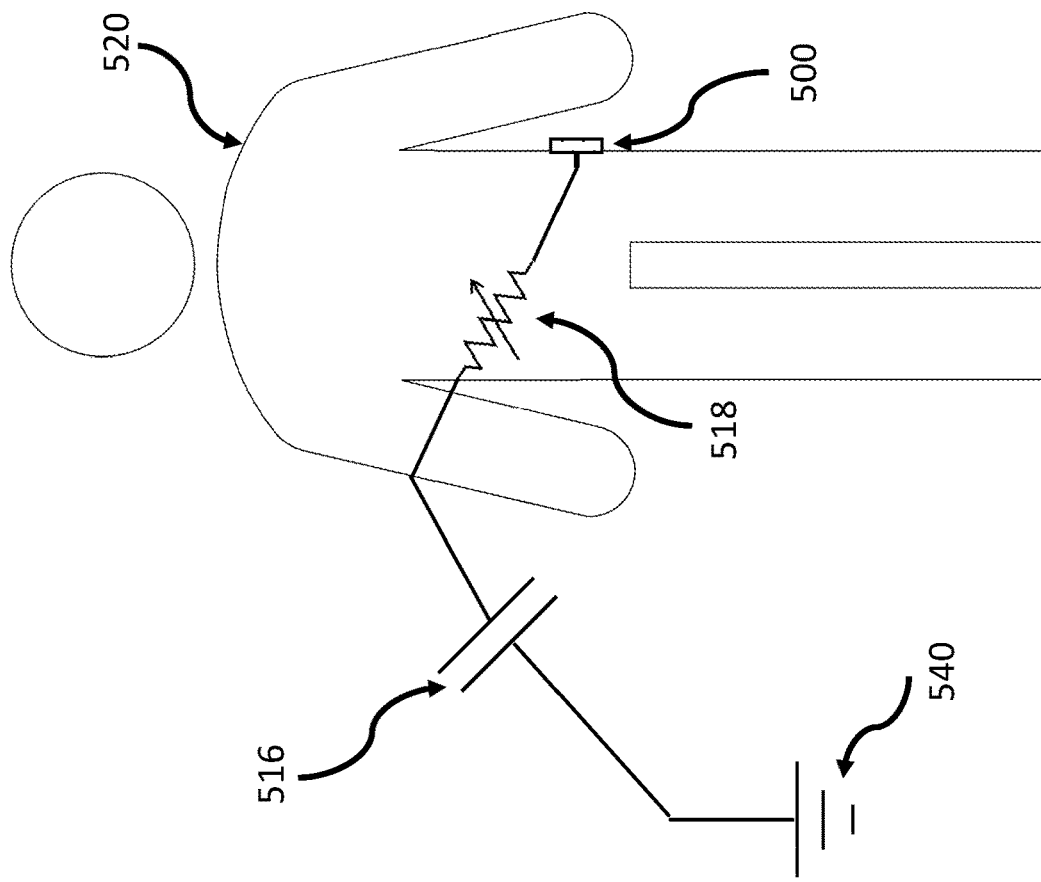
FIG. 5A shows an exemplary wearable drug delivery device worn by a person, in accordance with some embodiments of the disclosure.

FIG. 5A shows an exemplary wearable drug delivery device 500 worn by a person 520, in according with some embodiments of the disclosure. FIG. 5B shows circuit components including the exemplary wearable drug delivery device 500, in accordance with some embodiments of the disclosure.

FIG. 5A shows the wearable drug delivery device 500 worn by a person 520, and also shows the impedance 518, the capacitance 516 of the body to the rest of the world (~100-1000 pF), and the ground 540. The impedance 518 depends on penetration of the cannula of the drug delivery device 500, as described above. As the cannula of the drug delivery device 500 penetrates the body 520, the effective circuit components change due to change in the coupling from the cannula to the rest of the body 520. This in turn changes the charge as measured by the amplifier 532 of the self-capacitance measuring system 530. As described above with respect to FIGS. 2 and 4, the self-capacitance measuring system 530 also includes an additional electrical component module 550 and a voltage pulse 534.

According to various aspects, a more precise determination of the depth of the cannula (or needle) as well as the angle of insertion can be made by using extra electrodes. In particular, using extra electrodes, the mutual capacitance technique can be used to determine cannula depth and insertion angle. In one example, a voltage pulse is provided via a current restricting network and the change in charge is measured on the electrodes.

Figure 6:
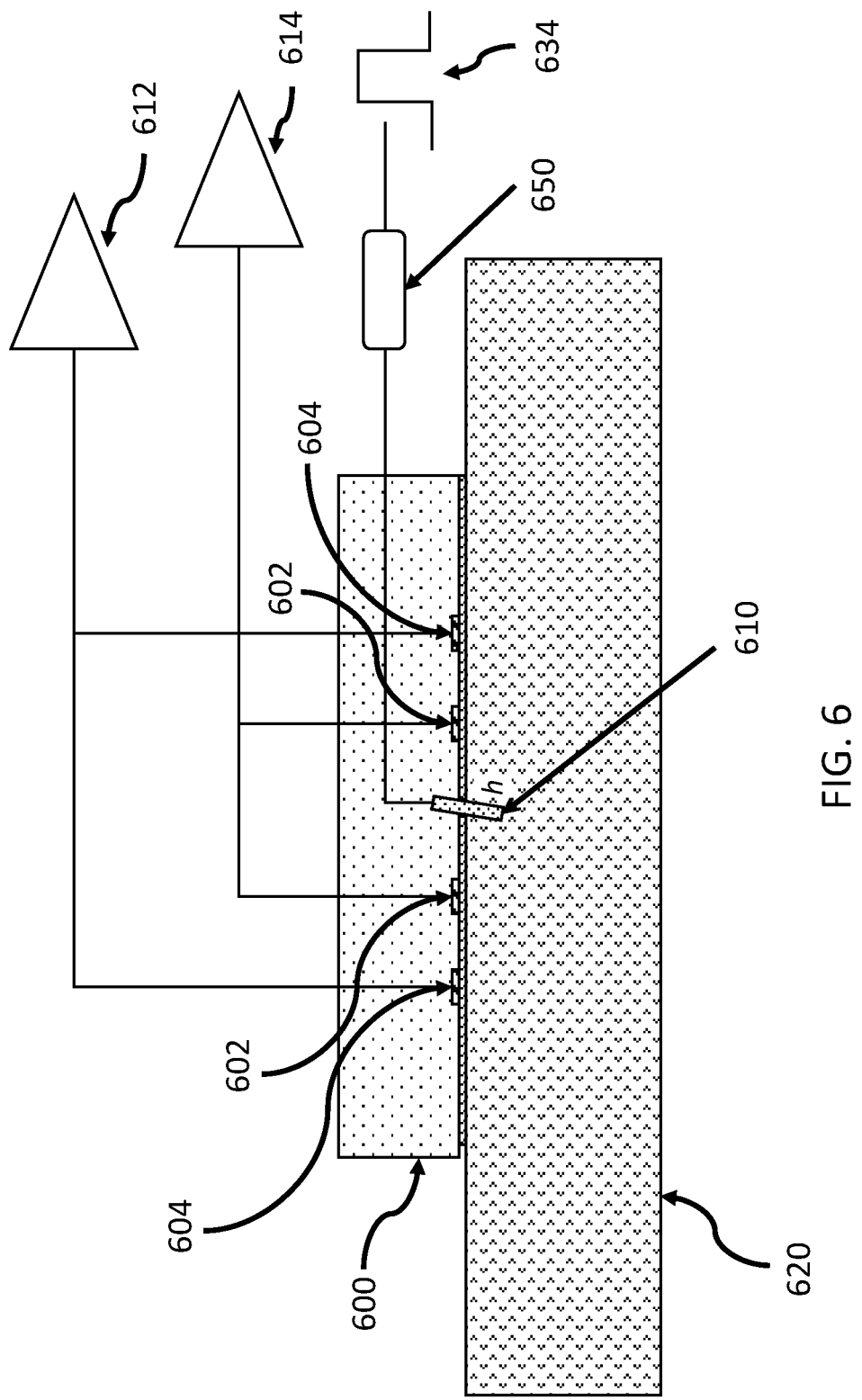
FIG. 6 shows an exemplary wearable drug delivery device including electrodes and a mutual-capacitance measuring system, in accordance with some embodiments of the disclosure.

FIG. 6 shows an exemplary wearable drug delivery device 600 including first 602 and second 604 electrodes and a mutual-capacitance measuring system, in accordance with some embodiments of the disclosure. The mutual capacitance measuring system includes a first amplifier 612, a second amplifier 614, an additional electrical component 650 and a voltage pulse 634. The capacitance $C_1$ from the first electrode 602 to the cannula 610 increases as the cannula 610 is inserted into the tissue 620. The capacitance $C_2$ from the second electrode 604 to the cannula similarly increases as the cannula 610 is inserted into the tissue 620.

Due to differences in the distance between the first electrode 602 and the cannula 610 and the distance between the second electrode 604 and the cannula 610, the capacitance $C_1$ as a function of cannula 610 depth changes differently from the capacitance $C_2$ as a function of cannula 610 depth. Thus, for example, the ratio of the capacitance $C_1$ to the capacitance $C_2$ can be related to the depth of cannula 610 insertion. In general, a function for the cannula 610 depth can be empirically derived based on the measurement of the capacitances $C_1$ and $C_2$.

Figure 7A:
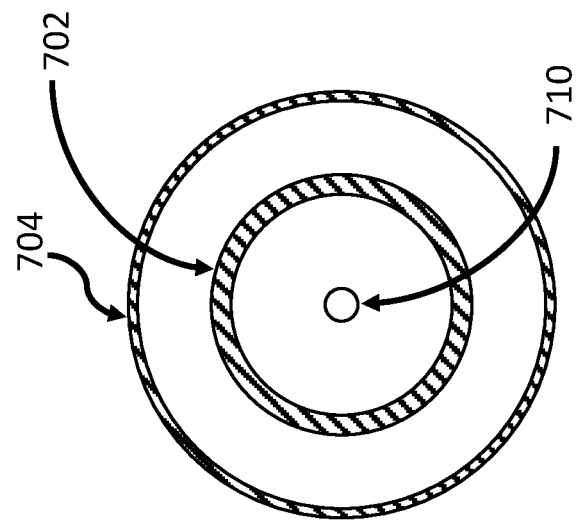
FIGS. 7A and 7B show exemplary electrode configurations for a drug delivery device, in accordance with some embodiments of the disclosure.
Figure 7B:
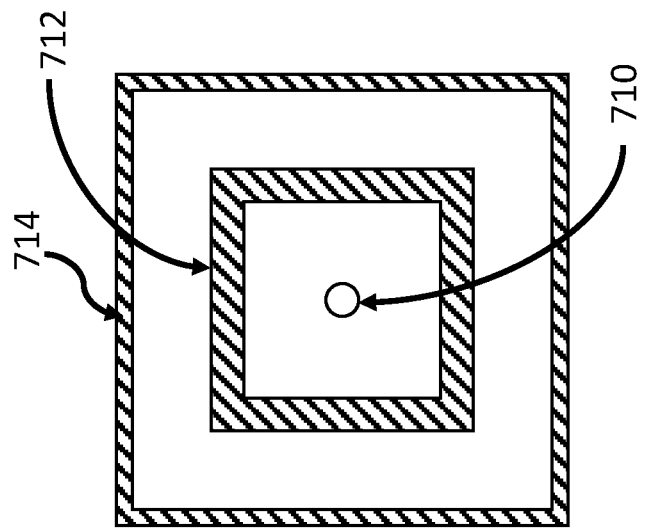

FIGS. 7A and 7B show exemplary electrode configurations for a drug delivery device, in accordance with some embodiments of the disclosure. FIG. 7A shows an electrode configuration having first 702 and second 704 circular concentric electrodes. The cannula 710 is positioned in the center of the first circular electrode 702, and there is a space between the cannula 710 and the first electrode 702. The second circular electrode 704 is positioned outside of the first circular electrode 702, and there is a space between the first electrode 702 and the second electrode 704.

According to some implementations, typical cannula depths are of the order of 4-6 mm. In one example, the distance between the first electrode 602 and the cannula 610 is between about 3 mm and about 5 mm. In one example, the distance between the second electrode 604 and the cannula 610 is between about 8 mm and about 12 mm.

FIG. 7B shows an electrode configuration having first 712 and second 714 square electrodes. The cannula 710 is positioned in the center of the first square electrode 712, and there is a space between the cannula 710 and the first electrode 712. The first square electrode 712 is positioned in the center of the second square electrode 714, and there is a space between the first electrode 712 and the second electrode 714.

According to various implementations, a different choice for geometries of the first and second electrodes produces a different distance function of the two capacitances $C_1$ and $C_2$. Many different electrode shapes are possible. Furthermore, according to various implementations, the area of each of the first and second electrodes can be designed to produce close to a unity ratio for a selected penetration depth. Implementing such a design allows the two amplifiers to be used with the same gain settings, which can make the measurement easier.

Figure 8:
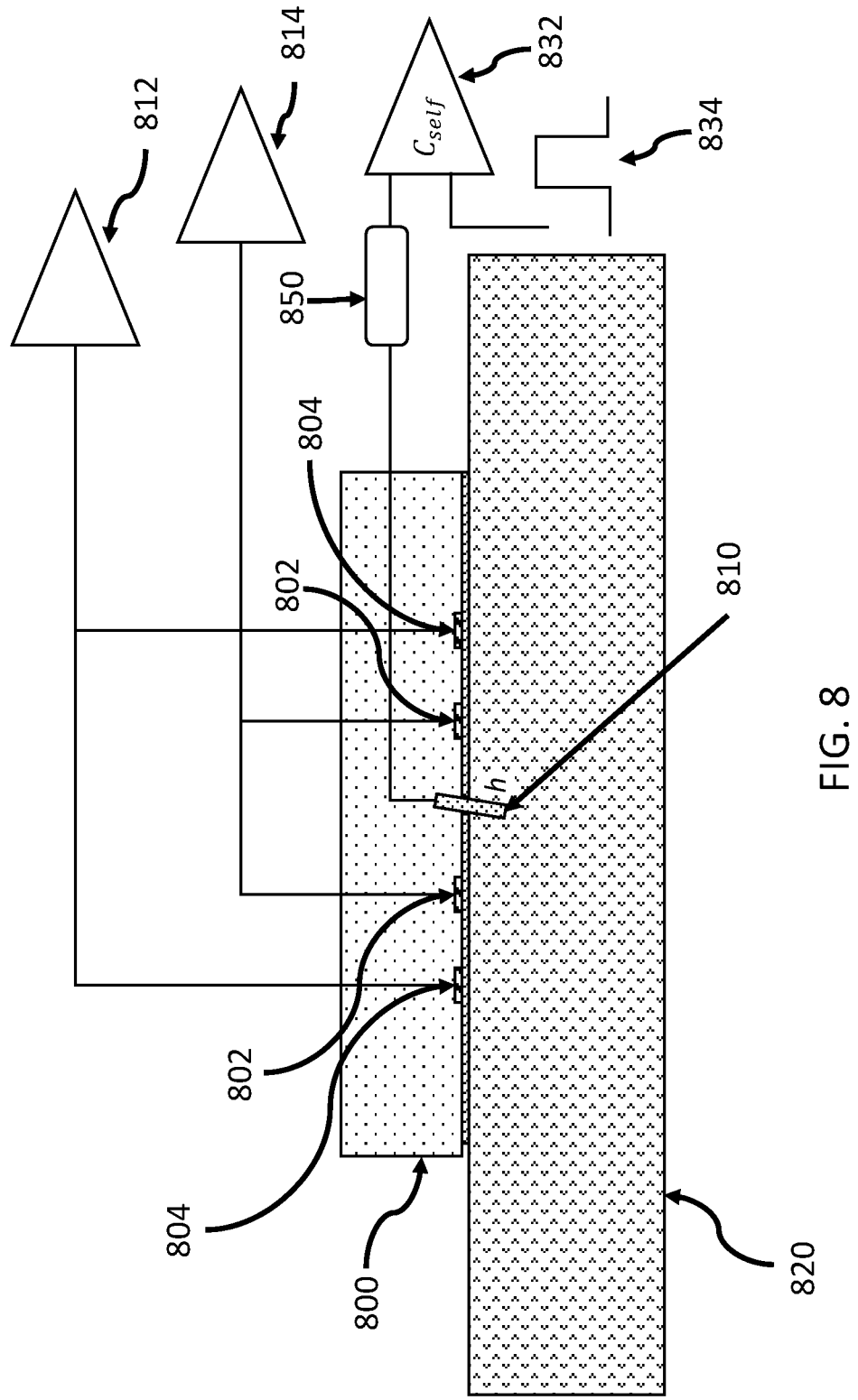
FIG. 8 shows an exemplary wearable drug delivery device including electrodes and a self-capacitance and a mutual capacitance measuring system, in accordance with some embodiments of the disclosure.

According to various implementations, in the mutual-capacitance measurement case, the cannula is given a voltage pulse while change in the charge is measured at the electrodes. Thus, the voltage pulse can be provided either directly through the current restricting network or thru the self-capacitance measuring amplifier. FIG. 8 shows an exemplary wearable drug delivery device 800 including first 802 and second 804 electrodes, first 814 and second 812 amplifiers, and a self-capacitance and a mutual capacitance measuring system, in accordance with some embodiments of the disclosure. FIG. 8 shows the provision of voltage pulse 834 through the self-capacitance measuring amplifier 832. FIG. 8 also shows an additional electrical component 850. Additionally, FIG. 8 illustrates a system that can simultaneously take measurements of self-capacitance and mutual-capacitance.

According to various implementations, depth of penetration can be determined using the mutual capacitance technique measured using only one mutual-capacitance measuring electrode. Combining mutual-capacitance and self-capacitance measurements together can provide a more accurate determination of the cannula depth.

Figure 9:
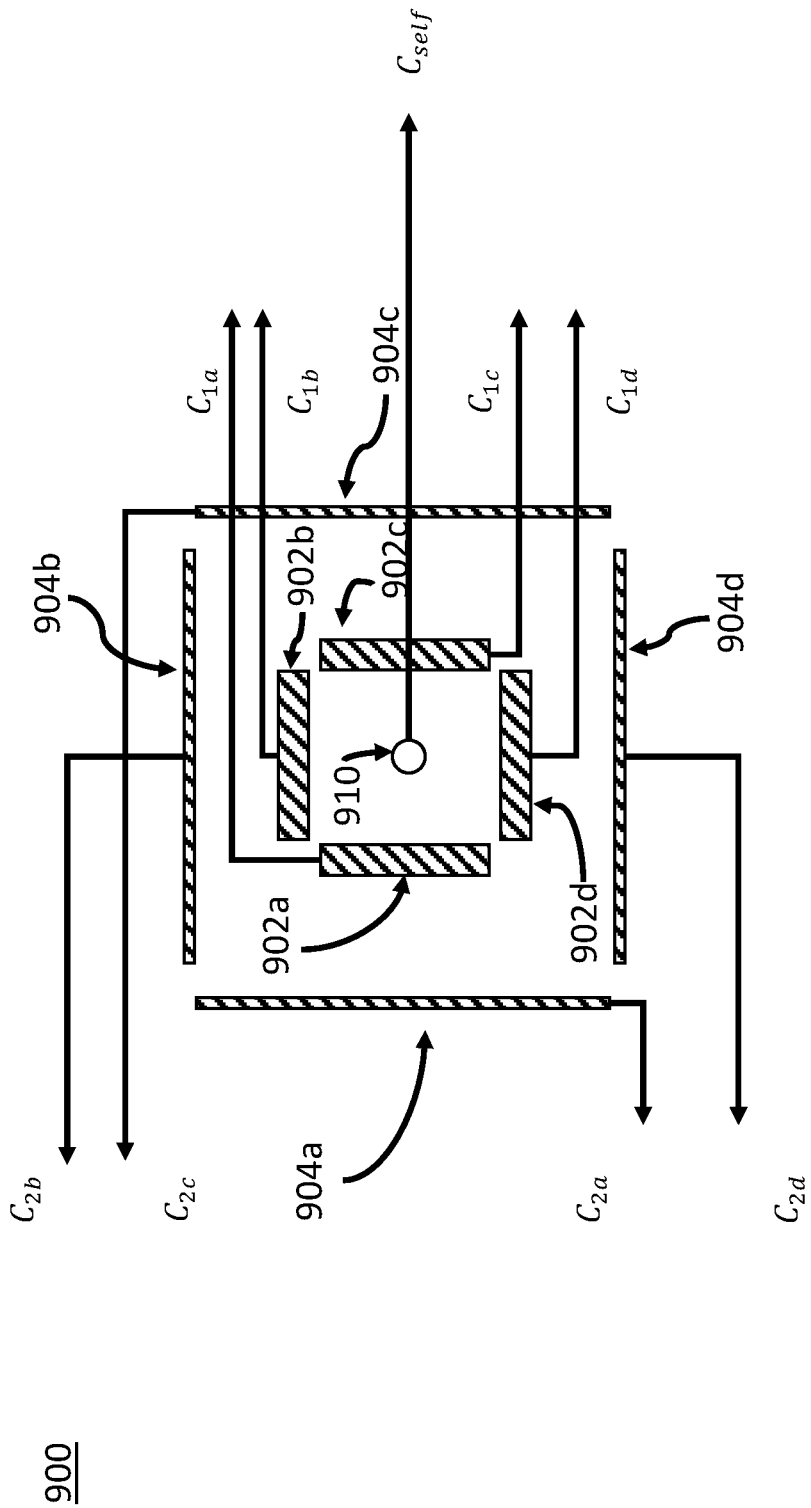
FIG. 9 shows an exemplary electrode configuration for a drug delivery device in which the first and second electrodes are each split into four distinct parts, in accordance with some embodiments of the disclosure.

FIG. 9 shows an exemplary electrode configuration 900 for a drug delivery device including a cannula 910 and in which the first and second electrodes are each split into four distinct parts, in accordance with some embodiments of the disclosure. In particular, the first electrode is split into first 902a, second 902b, third 902c, and fourth 902d parts. The capacitance of each of the first 902a, second 902b, third 902c, and fourth 902d parts is measured separately. Thus, there are four capacitance measurements from the first electrode: the first part of the first electrode 902a has a first capacitance $C_{1a}$, the second part of the first electrode 902b has a second capacitance $C_{1b}$, the third part of the first electrode 902c has a third capacitance $C_{1c}$, and the fourth part of the first electrode 902d has a fourth capacitance $C_{1d}$.

Similarly, the second electrode is split into first 904a, second 904b, third 904c, and fourth 904d parts. The capacitance of each of the first 904a, second 904b, third 904c, and fourth 904d parts is measured separately. Thus, there are four capacitance measurements from the second electrode: the first part of the second electrode 904a has a fifth capacitance $C_{2a}$, the second part of the second electrode 904b has a sixth capacitance $C_{2b}$, the third part of the second electrode 904c has a seventh capacitance $C_{2c}$, and the fourth part of the second electrode 904d has an eighth capacitance $C_{2d}$.

As shown in FIG. 9, the cannula 910 is positioned in the center of the four parts 902a, 902b, 902c, 902d of the first electrode, and in the center of the four parts 904a, 904b, 904c, 904d of the second electrode. Thus, when the cannula 910 is perpendicular to the plane formed by the eight electrodes 902a, 902b, 902c, 902d, 904a, 904b, 904c, 904d, the capacitances $C_{1a}$, $C_{1b}$, $C_{1c}$, $C_{1d}$ of the four parts 902a, 902b, 902c, 902d of the first electrode are all equal, and the capacitances $C_{2a}$, $C_{2b}$, $C_{2c}$, $C_{2d}$ of the four parts 904a, 904b, 904c, 904d of the second electrode are all equal.

In FIG. 8, the cannula 810 forms an angle to the plane of the first 802 and second 804 electrodes. The electrode closest to the tip of the cannula 810 will have higher capacitance. Thus, if the cannula 910 in FIG. 9 is inserted at an angle such as that shown in FIG. 8, the part of the first electrode closest to the tip of the cannula 910 will have the highest capacitance. From the measurement of the eight capacitances $C_{1a}$, $C_{1b}$, $C_{1c}$, $C_{1d}$, $C_{2a}$, $C_{2b}$, $C_{2c}$, $C_{2d}$, the angle of the needle can be determined, as well as the depth. Note that $C_1 = C_{1a} + C_{1b} + C_{1c} + C_{1d}$ and similarly $C_2 = C_{2a} + C_{2b} + C_{2c} + C_{2d}$.

The depth h of the cannula 910 can be derived from the ratio of the capacitances $$\frac{C_1}{C_2}.$$

For example:

$$h(C_1, C_2) = f\left(\frac{C_1}{C_2}\right) \quad (3)$$

The angle of the cannula along the x-axis of the cannula $\theta_x$ and the angle of the cannula along the y-axis of the cannula $\theta_y$ can be derived from a function such as:

$$\theta_x(C_{1c}, C_{1a}) = f_x\left(\frac{C_{1c} - C_{1a}}{C_{1c} + C_{1a}}\right) \quad (4)$$

$$\theta_y(C_{1b}, C_{1d}) = f_y\left(\frac{C_{1b} - C_{1d}}{C_{1b} + C_{1d}}\right) \quad (5)$$

Note that in some implementations, only one of the electrodes is split into multiple electrode parts. In some implementations, the angle information is derived by using a triangular three-part electrode geometry. In various implementations, an electrode can be split into two, three, four, five, six, seven, eight, nine, ten, or more than ten parts.

According to some examples, typical changes in the capacitance for accurate measurement have capacitance resolution in the femtofarad range. This is readily achievable in modern circuits.

The description above assumes an electrically conducting cannula. In some examples, the cannula may be made from steel. Many cannulas are made from plastics, such as Teflon, which are non-conducting. In some implementations, such as when a cannula is made from a non-conducting material, the cannula material may be coated with a conductive polymer or thin metallic layer to provide an electrical path. A highly resistive conductive layer can serve to restrict the currents flowing into the body and thus can become part of the current restricting network.

While the figures herein illustrate circuits in which the self-capacitance of the cannula and the mutual-capacitance of each electrode to the cannula is measured, the systems and methods contemplated herein are not restricted to these cases. According to various implementations, since capacitance measuring circuits are connected to each electrode, both the self-capacitance of each electrode and the mutual-capacitance of each electrode can be measured. This can occur either simultaneously or in quick succession. The self-capacitance of each electrode can provide information on whether the wearable drug delivery system is attached to the body.

Figure 10:
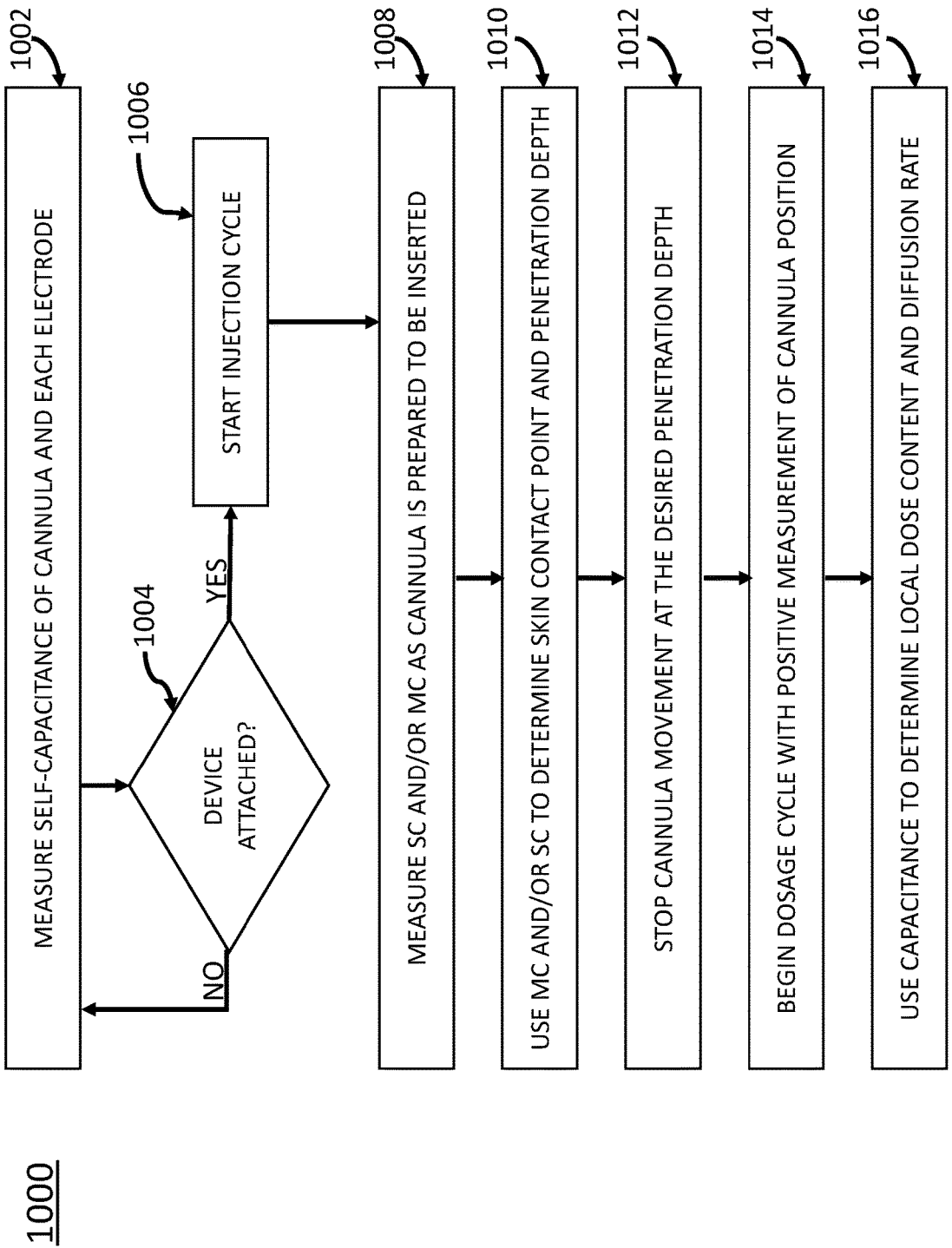
FIG. 10 illustrates a method for determining the depth and/or position of a cannula of a drug delivery device, in accordance with some embodiments of the disclosure.

FIG. 10 illustrates a method 1000 for determining the depth and/or position of a cannula of a drug delivery device, in accordance with some embodiments of the disclosure. At step 1002, the method 1000 starts with measuring the self-capacitance of each electrode, and measuring the self-capacitance of the cannula. At step 1004, the measured self-capacitances are used to determine whether the drug delivery device is still adjacent to a body. If the device is not attached to a body, the method returns to step 1002. If the device is attached to a body, as determined by the measured self-capacitance at each electrode and at the cannula, at step 1006, the injection cycle begins.

At step 1008, the self-capacitance and/or mutual capacitance of the cannula and one or more electrodes is measured. Then, as insertion of the cannula begins, at step 1010, the self-capacitance and/or mutual capacitance of the cannula and one or more electrodes continues to be measured. The self-capacitance and/or mutual capacitance of the cannula and one or more electrodes is monitored to determine skin contact point and, as penetration begins, the penetration depth. At step 1012, the cannula movement is stopped when the self-capacitance and/or mutual capacitance measurements indicate the cannula has reached a desired penetration depth. At step 1014, the dosage cycle begins as a drug or biologic is injected through the cannula. At step 1016, the self-capacitance and/or mutual capacitance continues to be measured while the drug or biologic is injected to determine local dose content and diffusion rate in the local tissue.

According to various implementations, the mutual-capacitance and self-capacitance measurements can provide information about the diffusion rate of a drug in the body. The information derived from the mutual-capacitance and self-capacitance measurements may depend on the dielectric constant of the injected biologic or the drug. After the drug is fully absorbed by the body, the measured capacitance will return to the pre-injection value. In fact, one can continue to measure the self-capacitance and/or mutual-capacitance. In some examples, continued self-capacitance and/or mutual-capacitance measurements can be used to keep the measurements within a pre-determined range. The pre-determined range may be determined such that the biologic and/or drug is injected at a rate at which the body can absorb the injected material, and not injected too rapidly for the body to absorb.

Figure 11:
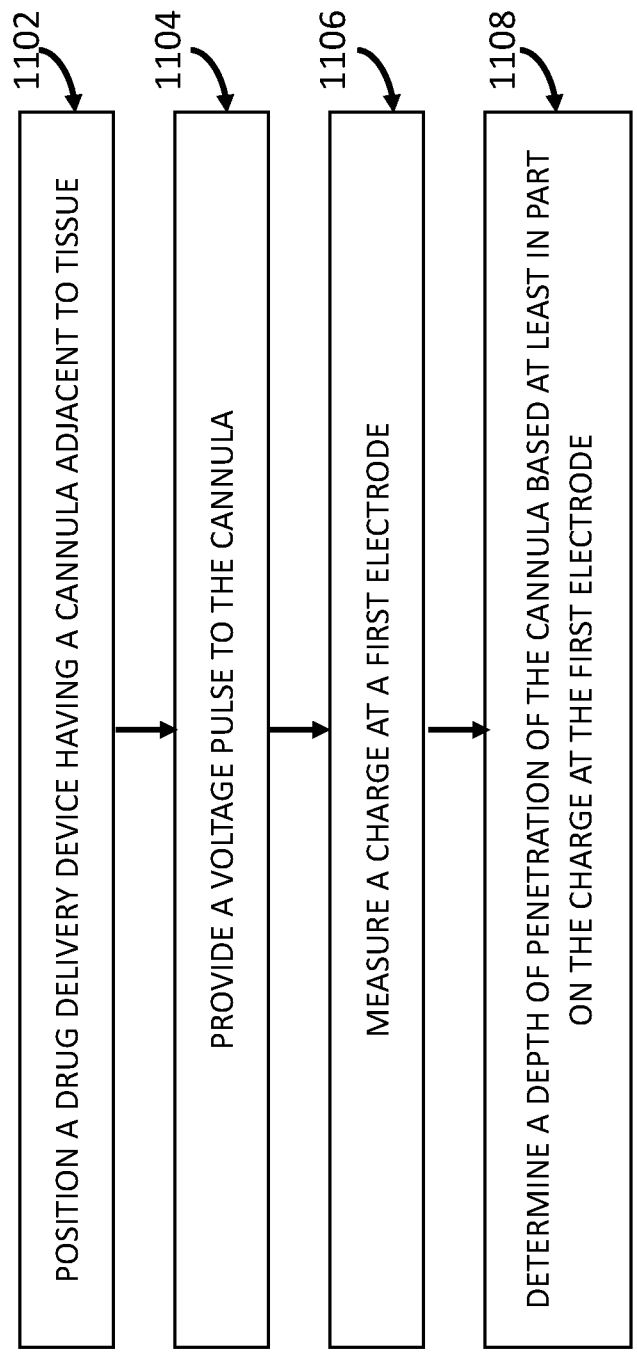
FIG. 11 illustrates a method for determining the depth of a cannula of a drug delivery device, in accordance with some embodiments of the disclosure.

FIG. 11 illustrates a method 1100 for determining the depth of a cannula of a drug delivery device, in accordance with some embodiments of the disclosure. At step 1102, a drug delivery device having a cannula is positioned adjacent to tissue. At step 1104, a voltage pulse is provided to the cannula. At step 1106, a charge is measured at a first electrode of the drug delivery device. At step 1108, a depth of penetration of the cannula is determined based at least in part on the charge at the first electrode.

In one or more embodiments, the electrodes comprise an electrically conductive electrolyte gel and a silver/silver chloride conductor. However, other materials and configurations are not beyond the scope of the present disclosure. For, example other non-dielectric intermediaries and conductive electrolyte gels can be used. Conversely, the use of dielectric compounds between the electrodes have been contemplated to reduce crosstalk.

In some embodiments, the electrodes are silver/silver chloride and the cannula Is metal. Yet, all conductive materials remain within the scope of the present disclosure. By way of example, either or both the electrodes or the needle can be a non-conductive (e.g., polymer) but coated with a conductive material, such as, a pure metal, alloy, or semiconductor. This coating can be performed by, for example but not limited to: direct metal deposition (DMD), laser metal deposition (LMD), thin-film deposition, chemical solution deposition (CSD), chemical bath deposition (CBD), chemical vapor deposition (CVD), plasma enhanced CVD (PECVD), atomic layer deposition (ALD), molecular layer deposition (MLD), physical vapor deposition (PVD), electroplating, and sputtering.

The conductive materials comprised by the electrodes and/or cannula include, but are not limited to: metal, metal alloys, compound metals, semi-conductors, conductive and semi-conductive polymers, conductive and semi-conductive composites, graphene, carbon nanotube, and graphite.

The present disclosure focuses on an exemplary wearable bolus injector. However, other suitable applications are not beyond the scope of the present invention. For example, the inventors have recognized that the current disclosure could be used in other medical procedures. Some examples of other medical procedures for which the systems and methods disclosed herein may be used include epidurals and medial branch blocks, where needle placement is so important that real time x-ray are frequently used to determine position. As such, these and other procedures and therapies remain in the scope of the present disclosure.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smart phone, a mobile phone, an iPad, or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A system for sensing cannula penetration depth in a drug delivery device, comprising:
    a cannula, configured for insertion into a tissue, wherein the cannula is conductive;
    a first circuit configured to provide a voltage pulse to the cannula;
    a first electrode, spaced apart from the cannula, wherein the first electrode surrounds the cannula;
    a mutual-capacitance circuit configured to measure a change in a first charge at the first electrode when the voltage pulse is provided to the cannula; and
    a processor configured to determine a depth of penetration of the cannula based at least in part on the change in the first charge at the first electrode.

2. The system of claim 1, wherein the mutual-capacitance circuit measures a first capacitance from the first electrode, and the processor is configured to determine the depth of penetration of the cannula based at least in part on the first capacitance.

3. The system of claim 1, further comprising a second electrode, spaced apart from the first electrode and the cannula, having a second charge.

4. The system of claim 3, wherein the mutual-capacitance circuit is further configured to measure a second capacitance from the second electrode, and the processor is further configured to determine the depth of penetration of the cannula based at least in part on the second capacitance.

5. The system of claim 1, wherein the first electrode is divided into at least two sections, and wherein the mutual-capacitance circuit determines a section-capacitance for each of the at least two sections.

6. The system of claim 5, wherein the processor is configured to determine an angle of penetration of the cannula based at least in part on the section-capacitances of the at least two sections.

7. The system of claim 1, wherein the cannula comprises a conductive metal.

8. The system of claim 1, wherein the cannula comprises a non-conducting material and is coated with a layer of conducting material.

9. The system of claim 1, further comprising a self-capacitance circuit configured to measure a change in cannula capacitance, wherein the processor is further configured to determine the depth of penetration of the cannula based at least in part on the cannula capacitance.

10. The system of claim 1, wherein the electrode is one of circular and polygonal.

11. A method for determining penetration depth of a cannula, comprising:
    positioning a drug delivery device including the cannula adjacent to tissue;
    providing a voltage pulse to the cannula;

measuring a charge at a first electrode of the drug delivery device when the voltage pulse is provided, wherein the first electrode surrounds the cannula;

measuring a second charge at a second electrode, wherein the second electrode is spaced apart from the first electrode and the cannula; and determining a depth of penetration of the cannula based at least in part on the charge at the first electrode.

12. The method of claim 11, wherein determining the depth of penetration of the cannula is based at least in part on the second charge at the second electrode.

13. The method of claim 11, further comprising:
determining a first capacitance from the first electrode to the cannula,
determining a second capacitance from the second electrode to the cannula, and
determining the depth of penetration based at least in part on the first and second capacitances.

14. The method of claim 11, further comprising:
measuring a change in cannula capacitance, and
determining the depth of penetration of the cannula based at least in part on the change in cannula capacitance.

15. The method of claim 11, further comprising:
measuring a self-capacitance of the first electrode, and
determining whether the drug delivery device is positioned adjacent to tissue, based at least in part on the self-capacitance of the first electrode.

16. The method of claim 11, further comprising determining an angle of penetration of the cannula.

17. A drug delivery apparatus for injecting a drug into tissue comprising:
a cannula, configured for insertion into the tissue, wherein the cannula is conductive;
a self-capacitance measuring circuit connected to the cannula for measuring a self-capacitance of the cannula, wherein the self-capacitance measuring circuit includes an amplifier and is configured to provide a voltage pulse, and wherein the amplifier is connected to the cannula and measures a charge from the cannula, wherein the amplifier measures the charge from the cannula when the voltage pulse is provided; and
a processor configured to determine the depth of penetration of the cannula based on the self-capacitance of the cannula.

18. The apparatus of claim 17, further comprising at least one of a series resistor and a capacitor, connected between the cannula and the amplifier.

19. The apparatus of claim 17, further comprising a mutual-capacitance measuring circuit.

20. The apparatus of claim 19, further comprising a first electrode, wherein the mutual-capacitance circuit measures a capacitance at the first electrode and the processor is further configured to determine the depth of the cannula based at least in part on the capacitance at the first electrode.

* * * * *